United States Patent [19]

Uzan

[11] 4,208,417
[45] Jun. 17, 1980

[54] INDOLE DERIVATIVES AND THEIR USE AS ANXIOLYTICS

[75] Inventor: André V. Uzan, Paris, France

[73] Assignee: Pharmindustrie, Gennevilliers, France

[21] Appl. No.: 920,598

[22] Filed: Jun. 29, 1978

[51] Int. Cl.² .......................................... A61K 31/445
[52] U.S. Cl. .................................................. 424/267
[58] Field of Search ......................................... 424/267

[56] References Cited
U.S. PATENT DOCUMENTS 4,064,255 12/1977 Champseix et al. ................ 424/267

Primary Examiner—Stanley J. Friedman

Attorney, Agent, or Firm—Beveridge, DeGrandi, Kline & Lunsford

[57] ABSTRACT

Compositions containing indole derivatives of the formula:

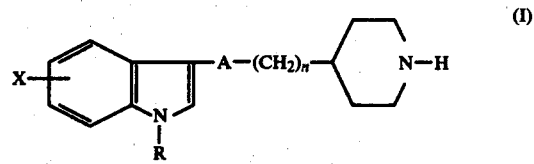

are strongly active as $^3$H-diazepam displacers and are consequently useful as anxiolytics.

10 Claims, No Drawings

INDOLE DERIVATIVES AND THEIR USE AS ANXIOLYTICS

BACKGROUND OF THE INVENTION

1. Field of the Invention

The anxiolytic activity of benzodiazepines is well known. The presence of brain specific benzodiazepine receptors in membranes from the rat brain is also well established (cf. Squires, R. F. et al., Nature 266 (1977), page 732).

Highly significant correlations between the affinities of various benzodiazepines for the benzodiazepine receptor site in the rat brain on the one hand and clinically predictive pharmacological activities in mammals on the other hand, strongly suggest that the benzodiazepine receptor in vitro is related to a physiologically relevant receptor for benzodiazepines in vivo.

2. Description of the Prior Art

Until now the binding site for benzodiazepine ($^3$H-diazepam) in the rat brain has been considered as highly specific for benzodiazepines, since none of the non-benzodiazepine substances demonstrated significant efficacy as $^3$H-diazepam displacers. This efficacy is measured by $K_i$ values in micro moles calculated by using the equation:

$$K_i = IC_{50}[(1+C)K_D]$$

wherein:
C = the concentration of $^3$H-diazepam,
$K_D$ = the affinity constant = 2.74 $\mu$M, and
$IC_{50}$ = the concentration causing 50% inhibition of $^3$H-diazepam binding.

Non-benzodiazepines were considered up to now as having no significant affinity for $^3$H-diazepam binding site, since their $K_i$ is higher than 100 $\mu$M. For example, Braestrup and Squires in the European Journal of Pharmacology, 48 (1978) 263–270 at page 268 disclose that they did not fine any compounds other than benzodiazepines with significant affinity for the $^3$H-diazepam binding site ($K_i > 0.1$ mM).

SUMMARY OF THE INVENTION

It has now been found, according to the present invention, that compounds having a chemical structure different from that of the benzodiazepines are strongly active as $^3$H-diazepam displacers and are consequently useful as anxiolytics.

DESCRIPTION OF THE PREFERRED EMBODIMENTS

The compounds according to the present invention may be represented by the following formula:

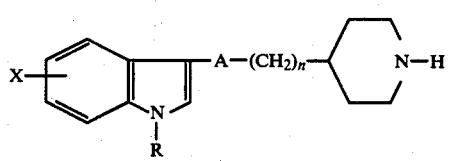

(I)

in which R is hydrogen, an alkyl group having 1 to 4 carbon atoms or an aralkyl group of which the alkyl contains 1 or 2 carbon atoms; X is hydrogen, alkyl, alkoxy or alkylthio, the alkyl of each containing from 1 to 4 carbon atoms, or a halogen atom; A is —CO— or —CH$_2$—; and n is 1 to 2.

Compositions based on these compounds are effective for treating mammals afflicted with depression. They have been proposed for this treatment in U.S. Pat. No. 4,064,255 filed Apr. 26, 1976 and issued Dec. 20, 1977 fpr "Compositions Containing Indole Derivatives and Their use in Pharmacology" (Inventors: Alain A. Champseix et al.), and said patent is incorporated herein in its entirety by reference.

It has now surprisingly been found that, in addition to their properties as antidepressants, they have a strong affinity for benzodiazepine receptor and are capable of displacing $^3$H-diazepam binding sites which confers on these products the property and ability to treat anxiety states.

Anxiolytic Properties

The anxiolytic activity of the compounds of formula (I) was demonstrated in vitro using inhibition of specific $^3$H-diazepam binding to rat brain membranes according to the method of Möhler, H. et al., Life Sci., 20, 1977; page 2101. The entire disclosure of Möhler et al. is relied upon in this connection and is incorporated herein by reference.

The results listed in Table 1 below show that these products are characterized by a strong $^3$H-diazepam displacement potency. The examples of U.S. Pat. No. 4,064,255 wherein they are described are shown in the table.

Table 1

Inhibition Of Specific $^3$H-Diazepam Binding To Rat Brain Membranes

| PRODUCTS (Examples of U.S. Pat. No. 4,064,255) | $K_i$ (in $\mu$M) |
|---|---|
| Indolyl-3-(piperidyl-4-methyl)ketone (Example 1) | 43 |
| [(Methoxy-5 indolyl-3)-2 ethyl]-4 piperidine (Example 8) | 40 |
| [(Methyl-1 indolyl-3)-2 ethyl]-4 piperidine (Example 9) | 90 |
| [(Indolyl-3)-2 ethyl]-4 piperidine (Example 10) | 64 |
| (Indolyl-3 methyl)-4 piperidine (Example 11) | 90 |
| [(Chloro-5 indolyl-3)-2 ethyl]-4 piperidine (Example 12) | 37 |
| [(Indolyl-3)-3 propyl]-4 piperidine (Example 13) | 70 |
| [(Benzyl-1 indolyl-3)-2 ethyl]-4 piperidine (Example 14) | 33 |
| Imipramine | inactive |

The effectiveness of the compounds of the above formula in the test of Möhler does not correlate with an effectiveness in behavioral screening tests such as antagonism of foot shock-induced fighting in mice wherein benzodiazepines are active (cf. Tedeschi, R. E. et al., J. Pharmacol., 125 (1959), 28.). This discrepancy confers to the products of the invention an entirely new spectrum of activity that is anxiolytic effectiveness without sedative properties.

Toxological Properties

The following Table 2 contains values already given in U.S. Pat. No. 4,064,255 and supplies additional values obtained according to the same procedure.

Table 2

| Products Examples of U.S. Pat. No. 4,064,255 | I.V. | Acute Toxicity in Mice LD$_{50}$ (mg/kg) Orally |
|---|---|---|
| Example 1 | 47 | between 300 and 900 |
| Example 8 | 41 | 675 |
| Example 9 | 44 | 225 |
| Example 10 | 60 | 600 |
| Example 11 | 57 | 225 |
| Example 12 | 85 | 625 |

Table 2-continued

| Products Examples of U.S. Pat. No. 4,064,255 | Acute Toxicity in Mice LD$_{50}$ (mg/kg) | |
|---|---|---|
| | I.V. | Orally |
| Example 13 | 29 | 600 |
| Example 14 | 33 | 525 |

Therapeutic Applications

The products of formula I are useful not only in the symptomatic relief of tension but also in anxiety states resulting from stressful circumstances or whenever somatic complaints are concomitant of emotional factors. They are useful in psychoneurotic states manifested not only by depressive symptoms but also by tension, anxiety, apprehension or agitation.

Unlike benzodizepines which are well known as anxiolytics and sedatives, the compounds of formula I and their pharmaceutically acceptable salts are devoid of sedative effects. They act as psychic stimulants.

Pharmaceutical compositions containing the active compound are prepared as described in U.S. Pat. No. 4,064,255 and the methods of administration are the same.

The usual recommended dosage ranges from 50 mg to 300 mg of active substance a day, either as a single daily dose or preferably in divided doses, each unit dose ranging from 1 to 5 mg per kg of body weight. The entire remaining disclosure under the heading THERAPEUTIC APPLICATIONS in cols. 9 and 10 of said U.S. Pat. No. 4,064,255 are incorporated herein by reference in this connection.

What is claimed is:

1. A method of treating a mammal afflicted with an anxiety state comprising administering to said mammal a therapeutically effective amount of a composition comprising a compound of the formula:

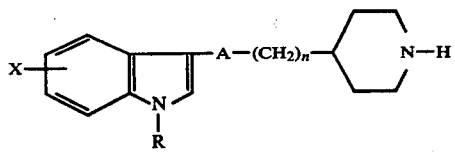

where R is hydrogen, an alkyl group having 1 to 4 carbon atoms or an aralkyl group of which the alkyl contains 1 to 2 carbon atoms; X is hydrogen, alkyl, alkoxy or alkylthio, the alkyl of each containing from 1 to 4 carbon atoms, or a halogen atom; A is —CO— or —CH$_2$—; or n is 1 to 2; and a pharmaceutically acceptable salt thereof; in a pharmaceutically acceptable carrier therefor.

2. A method as defined in claim 1 wherein said compound is indolyl-3(piperidyl-4 methyl)ketone.

3. A method as defined in claim 1 wherein said compound is [(methoxy-5 indolyl-3)-2 ethyl]-4 piperidine.

4. A method as defined in claim 1 wherein said compound is [(methyl-1 indolyl-3)-2 ethyl]-4 piperidine.

5. A method as defined in claim 1 wherein said compound is [(indolyl-3)-2 ethyl]-4 piperidine.

6. A method as defined in claim 1 wherein said compound is (indolyl-3 methyl)-4 piperidine.

7. A method as defined in claim 1 wherein said compound is [(chloro-5 indolyl-3)-2 ethyl]-4 piperidine.

8. A method as defined in claim 1 wherein said compound is [(indolyl-3)-3 propyl]-4 piperidine.

9. A method as defined in claim 1 wherein said compound is [benzyl-1 indolyl-3)-2 ethyl]-4 piperidine.

10. A method as defined in claim 1 wherein the composition is administered in an amount equivalent to a dosage from 50 to 300 mg a day.

* * * * *